(12) United States Patent
Xu et al.

(10) Patent No.: US 10,210,613 B2
(45) Date of Patent: Feb. 19, 2019

(54) MULTIPLE LANDMARK DETECTION IN MEDICAL IMAGES BASED ON HIERARCHICAL FEATURE LEARNING AND END-TO-END TRAINING

(71) Applicant: Siemens Healthcare GmbH, Erlangen (DE)

(72) Inventors: Daguang Xu, Princeton, NJ (US); Tao Xiong, Baltimore, MD (US); David Liu, Richardson, TX (US); Shaohua Kevin Zhou, Plainsboro, NJ (US); Mingqing Chen, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 79 days.

(21) Appl. No.: 15/591,157

(22) Filed: May 10, 2017

(65) Prior Publication Data

US 2017/0330319 A1    Nov. 16, 2017

Related U.S. Application Data

(60) Provisional application No. 62/335,436, filed on May 12, 2016.

(51) Int. Cl.
*G06T 7/00*    (2017.01)
*G06T 7/70*    (2017.01)
(Continued)

(52) U.S. Cl.
CPC .......... *G06T 7/0012* (2013.01); *A61B 5/4887* (2013.01); *G06N 3/08* (2013.01);
(Continued)

(58) Field of Classification Search
None
See application file for complete search history.

(56) References Cited

U.S. PATENT DOCUMENTS 6,324,532 B1 * 11/2001 Spence ................ G06K 9/3241
706/19
9,589,374 B1 * 3/2017 Gao ...................... G06T 11/008
(Continued)

OTHER PUBLICATIONS

Giannakidis et al., "Fast Fully Automatic Segmentation of the Severely Abnormal Human Right Ventricle from Cardiovascular Magnetic Resonance Images using a Multi-scale 3D Convolutional Neural Network", 2016 IEEE 12th International Conference on Signal-Image Technology & Internet-Based Systems, Nov. 28-Dec. 1, 2016, pp. 42-46.*

(Continued)

*Primary Examiner* — Matthew C Bella
*Assistant Examiner* — Jose Torres

(57) ABSTRACT

The present embodiments relate to detecting multiple landmarks in medical images. By way of introduction, the present embodiments described below include apparatuses and methods for detecting landmarks using hierarchical feature learning with end-to-end training. Multiple neural networks are provided with convolutional layers for extracting features from medical images and with a convolutional layer for learning spatial relationships between the extracted features. Each neural network is trained to detect different landmarks using a different resolution of the medical images, and the convolutional layers of each neural network are trained together with end-to-end training to learn appearance and spatial configuration simultaneously. The trained neural networks detect multiple landmarks in a test image iteratively by detecting landmarks at different resolutions, using landmarks detected a lesser resolutions to detect additional landmarks at higher resolutions.

17 Claims, 8 Drawing Sheets

(51) Int. Cl.
G06K 9/00 (2006.01)
G06N 3/08 (2006.01)
G06T 7/73 (2017.01)
A61B 5/00 (2006.01)
(52) U.S. Cl.
CPC .................. *G06T 7/70* (2017.01); *G06T 7/73* (2017.01); *G06T 2207/20076* (2013.01); *G06T 2207/20081* (2013.01)

(56) References Cited

U.S. PATENT DOCUMENTS

| | | | | |
|---|---|---|---|---|
| 9,830,529 | B2* | 11/2017 | Jetley | G06K 9/4671 |
| 2017/0278289 | A1* | 9/2017 | Marino | G06T 7/44 |
| 2018/0047159 | A1* | 2/2018 | Schlegl | G06K 9/6267 |
| 2018/0247107 | A1* | 8/2018 | Murthy | G06K 9/00147 |

OTHER PUBLICATIONS

Emad et al., "Automatic Localization of the Left Ventricle in Cardiac MRI Images Using Deep Learning", 2015 37th Annual International Conference of the IEEE Engineering in Medicine and Biology Society (EMBC), Aug. 25-29, 2015, pp. 683-686.*

Glocker, B., Feulner, J., Criminisi, A., Haynor, D.R. and Konukoglu, E., Oct. 2012. Automatic localization and identifcation of vertebrae in arbitrary field-of-view CT scans. In International Conference on Medical Image Computing and Computer-Assisted Intervention (pp. 590-598). Springer Berlin Heidelberg.

Badrinarayanan, V., Kendall, A. and Cipolla, R., 2015. Segnet: A deep convolutional encoder-decoder architecture for image segmentation. arXiv preprint arXiv:1511.00561.

Chen, H., Shen, C., Qin, J., Ni, D., Shi, L., Cheng, J.C. and Heng, P.A., Oct. 2015. Automatic localization and identification of vertebrae in spine ct via a joint learning model with deep neural networks. In International Conference on Medical Image Computing and Computer-Assisted Intervention (pp. 515-522). Springer International Publishing.

Chu, X., Ouyang, W., Li, H. and Wang, X., 2016. Structured feature learning for pose estimation. arXiv preprint arXiv:1603.09065.

Dou, Q., Chen, H., Jin, Y., Yu, L., Qin, J. and Heng, P.A., Oct. 2016. 3d deeply supervised network for automatic liver segmentation from ct volumes. In International Conference on Medical Image Computing and Computer-Assisted Intervention (pp. 149-157). Springer International Publishing.

Glocker, B., Zikic, D., Konukoglu, E., Haynor, D.R. and Criminisi, A., Sep. 2013. Vertebrae localization in pathological spine CT via dense classification from sparse annotations. In International Conference on Medical Image Computing and Computer-Assisted Intervention (pp. 262-270). Springer Berlin Heidelberg.

Merkow, J., Kriegman, D., Marsden, A. and Tu, Z., 2016. Dense Volume-to-Volume Vascular Boundary Detection. arXiv preprint arXiv:1605.08401.

Payer, C., Stern, D., Bischof, H. and Urschler, M., Oct. 2016. Regressing Heatmaps for Multiple Landmark Localization Using CNNs. In International Conference on Medical Image Computing and Computer-Assisted Intervention (pp. 230-238). Springer International Publishing.

Ronneberger, O., Fischer, P. and Brox, T., Oct. 2015. U-net: Convolutional networks for biomedical image segmentation. In International Conference on Medical Image Computing and Computer-Assisted Intervention (pp. 234-241). Springer International Publishing.

Suzani, A., Seitel, A., Liu, Y., Fels, S., Rohling, R.N. and Abolmaesumi, P., Oct. 2015. Fast Automatic Vertebrae Detection and Localization in Pathological CT Scans—A Deep Learning Approach. In International Conference on Medical Image Computing and Computer-Assisted Intervention (pp. 678-686). Springer International Publishing.

Xie, S. and Tu, Z., 2015. Holistically-nested edge detection. In Proceedings of the IEEE International Conference on Computer Vision (pp. 1395-1403).

Yang, W., Ouyang, W., Li, H. and Wang, X., 2016. End-to-end learning of deformable mixture of parts and deep convolutional neural networks for human pose estimation. CVPR.

* cited by examiner

MULTIPLE LANDMARK DETECTION IN MEDICAL IMAGES BASED ON HIERARCHICAL FEATURE LEARNING AND END-TO-END TRAINING

CROSS-REFERENCE TO RELATED APPLICATIONS

The present patent document claims the benefit of U.S. Provisional Application No. 62/335,436, filed on May 12, 2016, which is hereby incorporated by reference in its entirety.

BACKGROUND

Image processing determines the location of a particular anatomical feature or body part from the medical image. Machine learning may be used to detect a landmark in a medical image. Machine learning involves training to distinguish the appearance of a landmark from the appearance of rest of the medical image. Relying on appearance may yield false positives, such as from variations in scanned image data, unusual patient pathologies, motion artifacts, image artifacts from metal implants, low doses during image acquisition and other noise. If the landmark is not in the field of view of the scanner, the trained classifier may identify an incorrect feature as the landmark (i.e., false positives).

One solution for minimizing false positives is to detect multiple landmarks and to use the spatial or geometric relationship between the landmarks to rule out false positives, such as with a voting scheme. Non-maximal suppression may be used, where "modes" of a distribution are selected as candidate locations. The combination of possible landmark configurations grows exponentially as the number of landmarks and candidate locations increases, requiring specialized models and/or algorithms. Markov Random Field (MRF) or Conditional Random Field (CRF) are specialized and may result in accurate landmark detection, but the analysis is complicated and computationally intensive, thus approximation techniques are often used when the landmark configuration and underlying graph has loops. Another example of a specialized model uses heuristic voting in which a small set of candidate locations vote on each other. MRF and CRF models and heuristic voting all suffer from false negatives. When a landmark is outside of the field of view, the aforementioned models may assign a "virtual" candidate location denoting the absence of a landmark, which may be selected in a false positive. Designing for virtual candidates is complex and may require assigning a probability on how likely a landmark is absent, which is empirical and may not be accurate.

SUMMARY

The present embodiments relate to detecting multiple landmarks in medical images. By way of introduction, the present embodiments described below include apparatuses and methods for detecting landmarks using hierarchical feature learning with end-to-end training. Multiple neural networks are provided with convolutional layers for extracting features from medical images and with another convolutional layers for learning spatial relationships between the extracted features. Each neural network is trained to detect different landmarks using different resolutions of the medical images, and the convolutional layers of each neural network are trained together with end-to-end training to learn appearance and spatial configuration simultaneously. The trained neural networks detect multiple landmarks in a test image iteratively by detecting landmarks at different resolutions, using landmarks detected at a lesser resolutions to detect additional landmarks at higher resolutions.

In a first aspect, a method of deep learning for multiple landmark detection is provided. The method includes receiving a plurality of training images and training a first deep neural network at a first resolution of the training images. Training the first deep neural network includes learning locations of a first plurality of landmarks and learning the spatial relationships between the locations of the first plurality of landmarks. The method also includes training a second deep neural network at a second resolution of the training images. Training the second deep neural network includes learning locations of a second plurality of landmarks and learning spatial relationships between the locations of the second plurality of landmarks.

In a second aspect, a system is provided for detecting multiple landmarks in medical image data. The system includes a scanner configured to capture medical image data, a processor and a memory that includes computer program code for one or more programs. With the processor, the memory and the computer program code are configured to cause the system to receive medical image data captured by the scanner, and to detect multiple landmarks in the medical image data at different resolutions of the medical image data using a trained first artificial agent and a trained second artificial agent.

In a third aspect, a method for multiple landmark detection is provided. The method includes receiving medical image data from a medical scanner and identifying a first subset of a plurality of landmarks from the medical image data at a first resolution using a first learned deep neural network. The method also includes identifying a second subset of the plurality of landmarks from the medical image data at a second resolution using a second learned deep neural network. The method further includes displaying a medical image from the medical image data identifying the identified first subset of landmarks and the identified second subset of landmarks.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EXEMPLARY EMBODIMENTS

Figure 1:
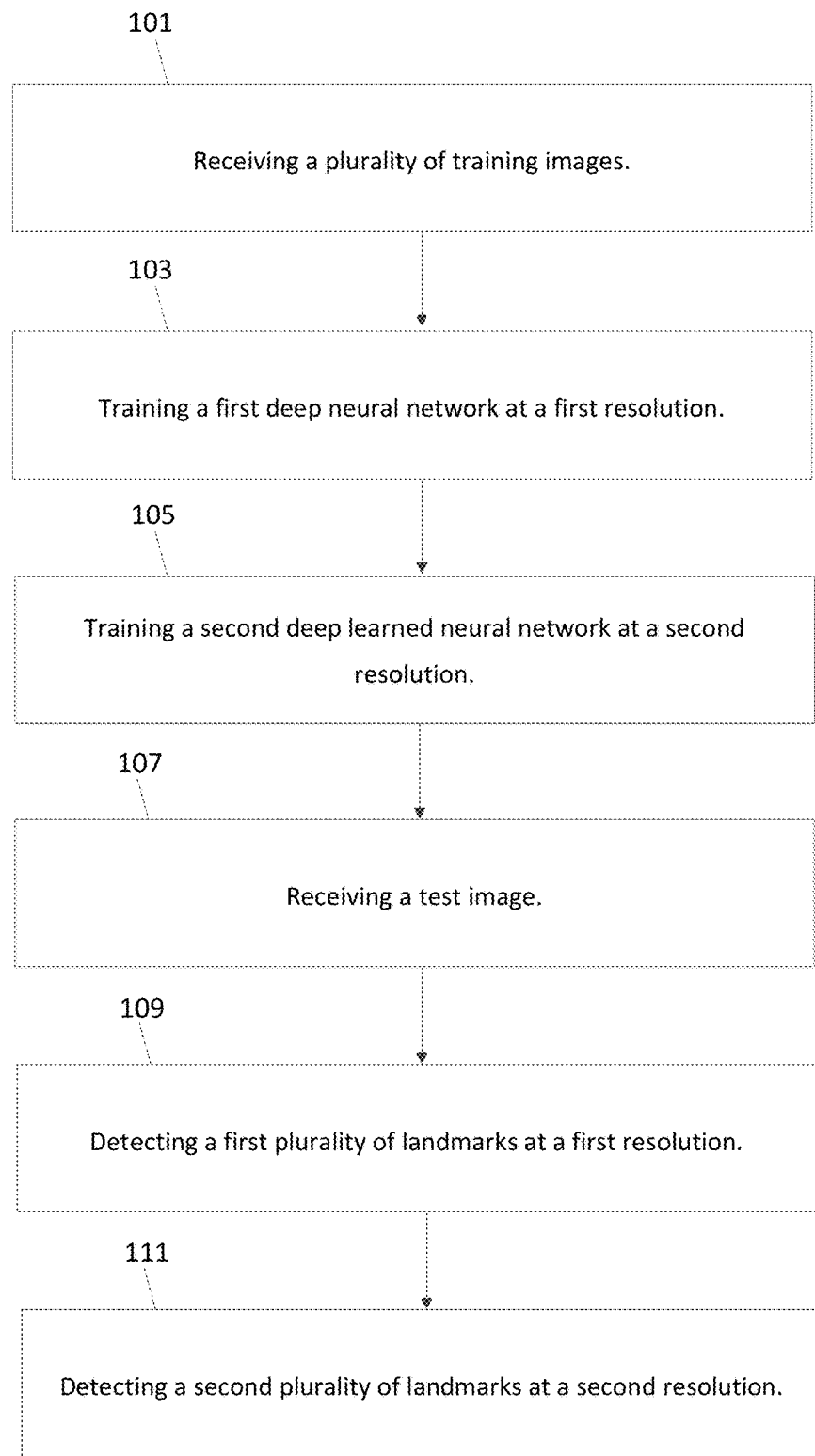
FIG. 1 illustrates a flowchart diagram of an embodiment of a method of deep learning for multiple landmark detection.

Landmark detection and labeling may be used in many clinical tasks, including pathological diagnosis, surgical planning and postoperative assessment. Specialized neural networks are provided to detect multiple landmarks in medical images. The neural networks include multiple layers of convolution, non-linear activations, spatial pooling and spatial unpooling to extract features from the medical images. The neural networks also include joint feature learning to map the spatial configuration of the features using multiple probability maps that interact with each other by passing information between probability maps. The feature extraction and joint feature mapping are trained simultaneously, providing end-to-end learning for the neural networks. The neural networks use the extracted features and spatial configurations to determine the true location of each landmark, ruling out false positives and negatives during the landmark detection.

A hierarchy of the neural networks is also established for detecting landmarks at different resolutions. A first neural network is trained at a lower resolution of the image to detect a subset of landmarks at the lower resolution. After the first subset of landmarks is determined, then a second neural network is trained at a higher resolution of the image to detect another subset of landmarks at the higher resolution. Any number of resolutions and corresponding neural networks may be used. With each increase in resolution, a denser set of landmarks is detected, providing an iterative, coarse-to-fine landmark detection process. The hierarchical framework of multiple neural networks may detect a large number of landmarks, such as several hundred landmarks (e.g., mesh points) for each anatomical feature (e.g., an organ of a patient). Any number of landmarks may be used, limited only by the image or volume (e.g., every pixel or voxel may be considered as a landmark).

Detecting landmarks using hierarchical feature learning and end-to-end training may minimize or eliminate false negatives during landmark detection. Instead of preselecting a set of candidate locations for each landmark, all potential candidate locations are considered during training by extracting features from analysis of each pixel or voxel, eliminating the need for non-maximal suppression. The speed and computational complexity of the landmark detection may be reduced as complexity is linearly related to the number of pixels or voxels considered at each resolution, rather than exponentially related to the number landmarks and the number of candidate locations for each landmark. Further, false positives for landmarks outside of the field-of-view may also be reduced or eliminated. By directly determining whether a landmark is absent, there is no need to designate "virtual" candidate locations to denote the absence of a landmark (e.g., outside of the field-of-view). For example, if a landmark is outside the field of view of an image, the landmark will be directly determined as being absent (e.g., with low probability score).

FIG. 1 illustrates a flowchart diagram of an embodiment of a method of deep learning for multiple landmark detection. The method is implemented by the system of FIG. 8 (discussed below), FIG. 9 (discussed below) and/or a different system. Additional, different or fewer acts may be provided. For example, the acts 107, 109 and 111 may be omitted to train the neural networks for landmark detection. As another example, acts 101, 103 and 105 may be omitted to test the image for a particular patient using already trained networks. The method is performed in the order shown. Other orders may be provided and/or acts may be repeated. For example, act 103 and/or 105 may be repeated to train additional deep neural networks, and act 109 and/or 111 may be repeated to detect another plurality of landmarks at a different resolution. Acts 107, 109 and 111 may also be repeated to detect landmarks from another test image. Further, acts 109 and 111 may be performed concurrently as parallel acts.

At act 101, a plurality of training images is received. The training images may be two-dimensional images or three-dimensional volumes. An image is used in the sense of scalar values that may be used to generate a display of the image or the displayed image itself. The training images may be imaging data captured using computed tomography (CT) or magnetic resonance imaging (MRI). Any imaging modalities and scanners may be used, such as ultrasound, x-ray, angiography, fluoroscopy, positron emission tomography, single photon emission computed tomography, or others. Alternatively, the training images may be synthetically generated without using a scanner. Landmarks in the training images may be labeled or annotated for machine learning (e.g., as ground truth data).

At act 103, a first deep neural network is trained at a first resolution. The first deep neural network is trained for landmark appearance and spatial configuration simultaneously using the plurality of training images. For example, the deep neural network learns a first plurality of landmarks at the first resolution of the training images and learns spatial relationships between landmarks. The first plurality of landmarks is a subset of the landmarks in the training images (e.g., a set of landmarks, pixels or voxels, available at a lesser resolution than the highest resolution of the training images).

Figure 2:
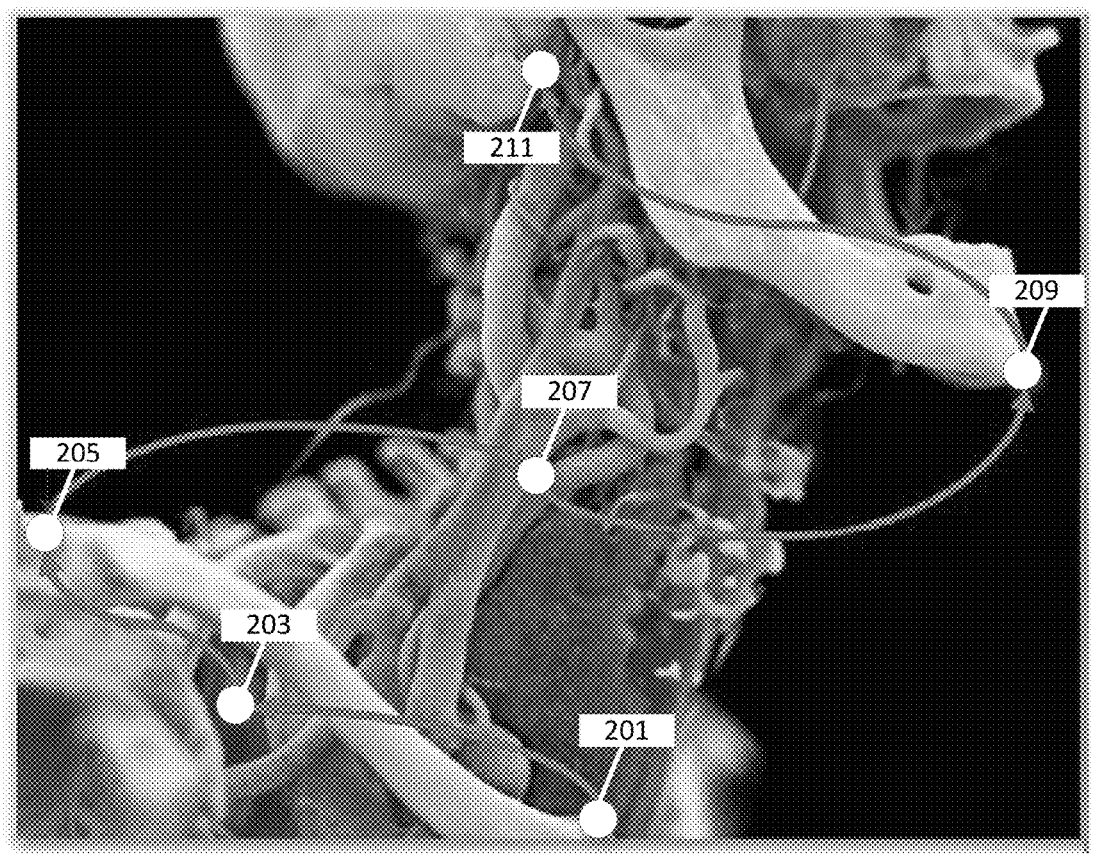
FIG. 2 illustrates an example of landmark appearance and spatial configuration.

FIG. 2 illustrates an example of landmark appearance and spatial configuration. The appearance of each landmark 201, 203, 205, 207, 209 and 211 are learned by the deep neural network using feature extraction. The spatial configuration between landmarks is simultaneously learned by the deep neural network using joint feature learning. For example, referring to landmarks 201 and 203, the deep neural network learns both the appearance of each landmark 201 and 203, as well as the relative location of landmark 203 to landmark 201. The neural network also learns the appearance of landmark 205 and the relative location of landmark 205 to landmark 203. The deep neural network learns the appearance and spatial configuration for each landmark. By training the deep neural network with both appearance and spatial configuration, the deep neural network may minimize or eliminate false positives and negatives by detecting landmarks by both appearance and relative location to one another.

The deep neural network includes two parts that are simultaneously trained (e.g., end-to-end training). The first part of the neural network includes multiple layers of convolutional, non-linear activations, spatial pooling and spatial unpooling for feature extraction. The second part of the neural network includes multiple landmark probability maps that interact with each other to map spatial relationships between the features.

Figure 3:
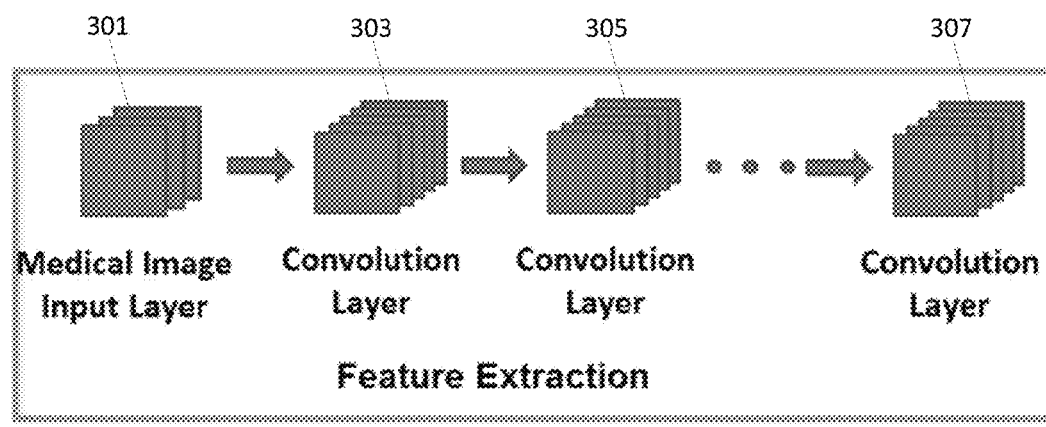
FIG. 3 illustrates an example of feature extraction with a deep neural network.

FIG. 3 illustrates an example of feature extraction with a deep neural network. The deep neural network includes a medical image input layer 301 for receiving training images during a training phase and for receiving a test image during landmark detection. The deep neural network also includes one or more convolutional layers 303, 305 and 307 for extracting features from the training images during training and the test image during landmark detection. The convolutional layers learn to extract features based on the appearance and/or the context of landmarks in each of the training images. The extracted features are used during joint feature learning for end-to-end training of appearance and spatial configuration.

Figure 4:
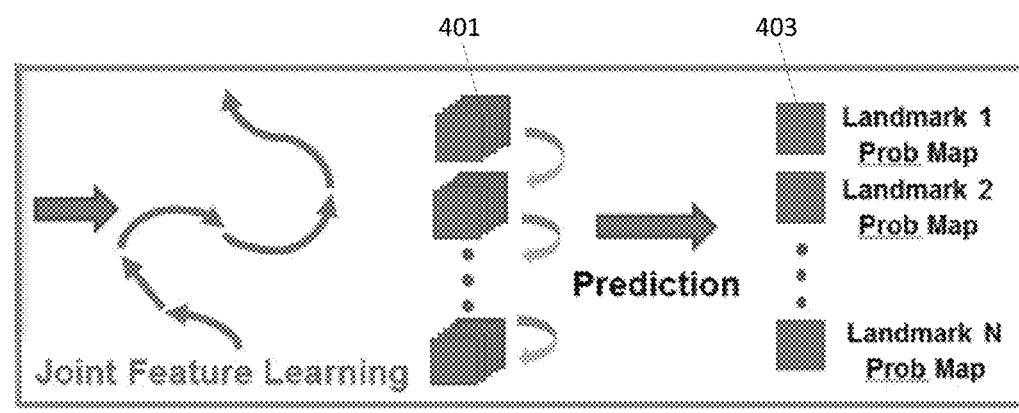
FIG. 4 illustrates an example of joint feature learning with a deep neural network.

FIG. 4 illustrates an example of joint feature learning with a deep neural network. One or more additional convolutional layers 401 are provided to map the spatial configuration and relationships between the extracted features from FIG. 3 using landmark probability maps 403. The landmark probability maps 403 are connected together and are predicted using inputs from other probability maps, based on spatial relationships between the landmarks.

For example, different probability maps are provided for each landmark. Each probability map is predicted by landmarks "voting" for the other landmarks, or "voting" for a subset of other landmarks (e.g., neighboring landmarks). The "voting" is performed by convolution operations of convolution layer 401 using a fixed sized filter (e.g., multiple operations that combine location networks using the convolution operations). For example, a location network predicts a location shift or relationship between extracted features, such as using feature maps. The fixed sized filter (e.g., a deformation filter) is learned by back-propagation using message passing between probability maps. The deformation filter for joint feature learning is trained together (e.g., end-to-end) with the appearance filters for feature extraction.

The "voting" may be performed iteratively. Initially, some probability maps have no or a low response to the ground truth landmark locations from the training images. In a series of iterations, layers of convolution are selectively connected to pass information (e.g., messages) between the layers to enhance the response of the probability maps to the ground truth landmark locations. The spatial relationships between landmarks are embedded in the convolutional layers, and various layers of convolution are selectively connected to pass messages based on how well the layers predict the locations of other landmarks. For example, messages are passed iteratively between neighboring landmarks in order to exchange information and optimize the overall probability distribution for the landmark detection. Message passing between landmark probability maps compensates for low or missing response in the landmark probability maps.

End-to-end training is provided by training the convolutional layers for feature extraction and joint feature learning simultaneously. The output of the deep neural network is the probability map providing a probability distribution for the location of each landmark within a given test image. If the probability distribution for a landmark is zero or below a threshold, then the neural network indicates that the landmark is not present in the test image.

Referring back to FIG. 1, at act 105, a second deep neural network is trained at a second resolution. The second deep neural network is trained for landmark appearance and spatial configuration simultaneously using the same plurality of training images at a higher resolution. For example, the deep neural network learns a second plurality of landmarks at a second resolution and learns spatial relationships between landmarks. The second plurality of landmarks are a different subset of the landmarks in the training images (e.g., a set of landmarks, pixels or voxels, available at a higher resolution than the resolution used by the first deep neural network). In this example, the second subset of landmarks identifies additional, different landmarks that may be combined with the first subset of landmarks to provide a large number of detected landmarks for display to a user.

The second deep neural network has the same or similar convolutional layers as depicted in FIG. 3 and FIG. 4. For example, the second deep neural network includes two parts that are simultaneously trained (e.g., end-to-end training). The first part of the neural network includes multiple layers of convolution, non-linear activations, spatial pooling and spatial unpooling for feature extraction. The second part of the neural network includes multiple landmark probability maps that interact with each other to map spatial relationships between the features.

The second deep neural network is trained to detect a second plurality of landmarks and spatial relationships between the second plurality of landmarks. A different landmark probability map is learned for each landmark, and the plurality of landmark probability maps simultaneously learned for each of the second plurality of landmarks using message passing between landmark probability maps of neighboring landmarks. The message passing between landmark probability maps of neighboring landmarks compensates for missing or low response information in each of the landmark probability maps.

The second plurality of landmarks is trained at the second resolution based on locations of the first plurality of landmarks at the first resolution. For example, the landmarks detected by the first deep neural network may be used as a starting point and/or as additional information for detecting additional landmarks at a higher resolution. For example, by leveraging information from the lower resolution, learning the second plurality of landmarks at a higher resolution only requires roughly the same computational complexity as learning the first plurality of landmarks at the lower resolution, even when detecting a larger number of landmarks at the higher resolution.

Acts 103 and/or 105 may be repeated to add additional deep neural networks trained at additional resolutions. Any number of deep neural networks may be provided for learning landmarks at various resolutions available from the training images. The deep neural networks are then used to iteratively detect landmarks in a training image at different resolutions from coarse-to-fine in acts 107, 109, and 111.

At act 107, a test image is received. The test image is captured using the same imaging modality as the plurality of training images. For example, the test image may be a CT or MRI image of a patient for a clinical task, such diagnosis, surgical planning, postoperative assessment, etc. Other imaging modalities may be used.

Figure 5:
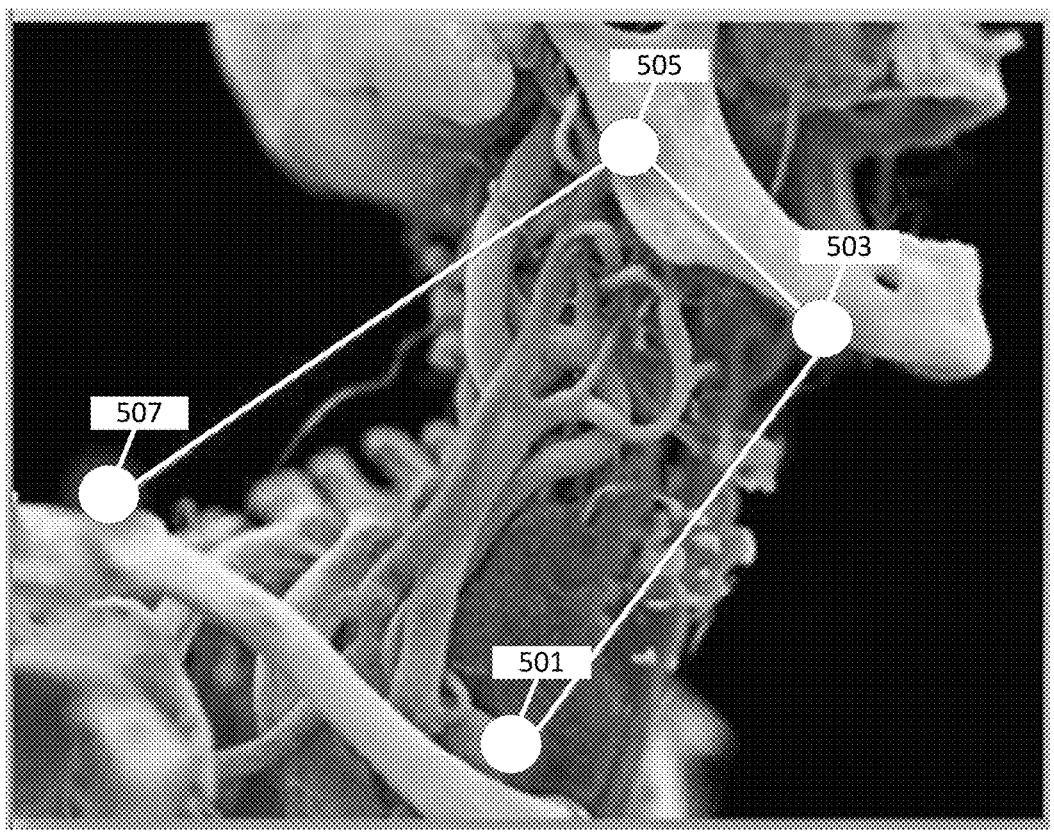
FIG. 5 illustrates an example of a first iteration of landmark detection.
Figure 6:
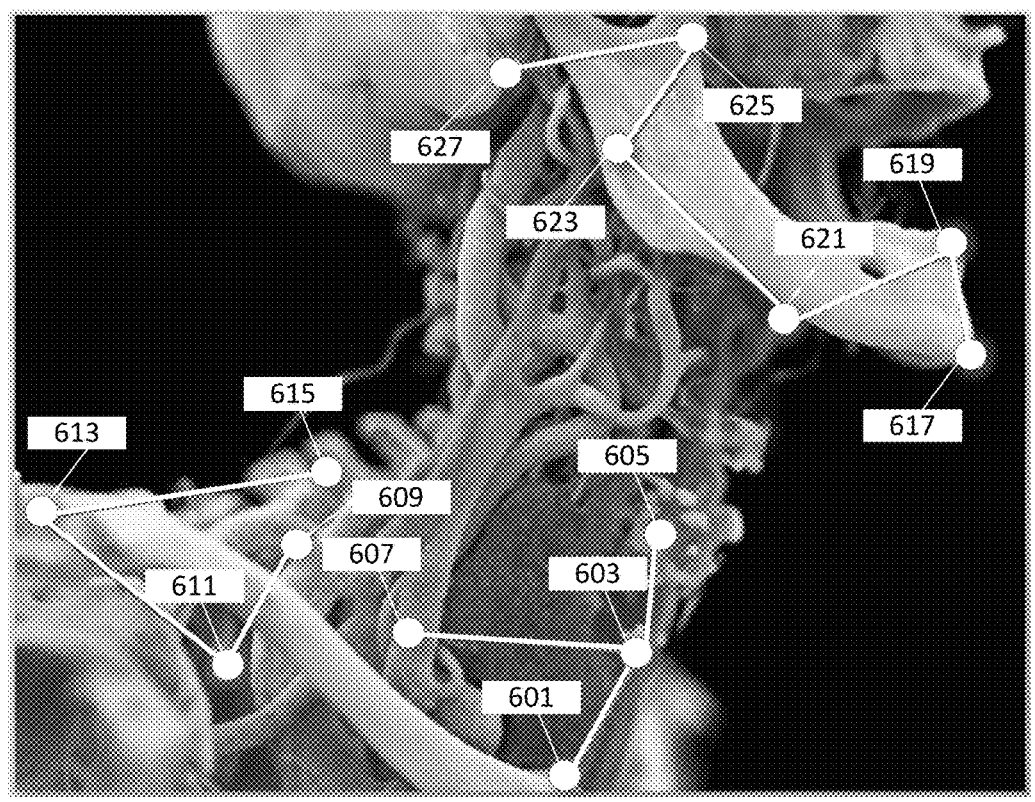
FIG. 6 illustrates an example of a second iteration of landmark detection.

At act 109, the first plurality of landmarks is detected in the test image using the first trained deep learned neural network. The first plurality of landmarks is detected using the test image at the first resolution (e.g., lesser or coarse resolution). FIG. 5 illustrates an example of a first iteration of landmark detection and FIG. 6 illustrates an example of a second iteration of landmark detection. For example, FIG. 5 shows the lower-resolution image used for detecting the first plurality of landmarks 501, 503, 505, 507 in act 109. In the lower resolution, only a subset of landmarks 501, 503, 505, 507 is detected. Once the subset of landmarks 501, 503, 505, 507 is detected, the method proceeds to detecting landmarks at a higher resolution (e.g., using larger number landmarks).

At act 111 of FIG. 1, the second plurality of landmarks is detected in the test image using the second trained deep learned neural network. The second plurality of landmarks is detected using the test image at the second resolution (e.g., greater or finer resolution). FIG. 6 shows the higher-resolution image used for detecting the second plurality of landmarks 601-627 in act 111. The same landmarks 501, 503, 505, 507 detected at the lower resolution may be re-detected at the higher resolution. Alternatively, only some or none are redetected and the higher resolution is used to add additional landmarks. In the examples of FIGS. 5 and 6, the landmarks 503 and 505 are detected at the higher resolution as landmarks 621 and 623 and the landmarks 501 and 507 are not redetected.

The landmarks 601-627 in higher resolution may form a plurality of subsets of landmarks, and detecting each subset of landmarks uses roughly the same computational complexity as the subset of landmarks detected at the lower resolution. As depicted in FIG. 5 and FIG. 6, multiple landmarks are detected in two or more iterations in a hierarchal process, from coarse resolutions to finer resolutions.

Figure 7:
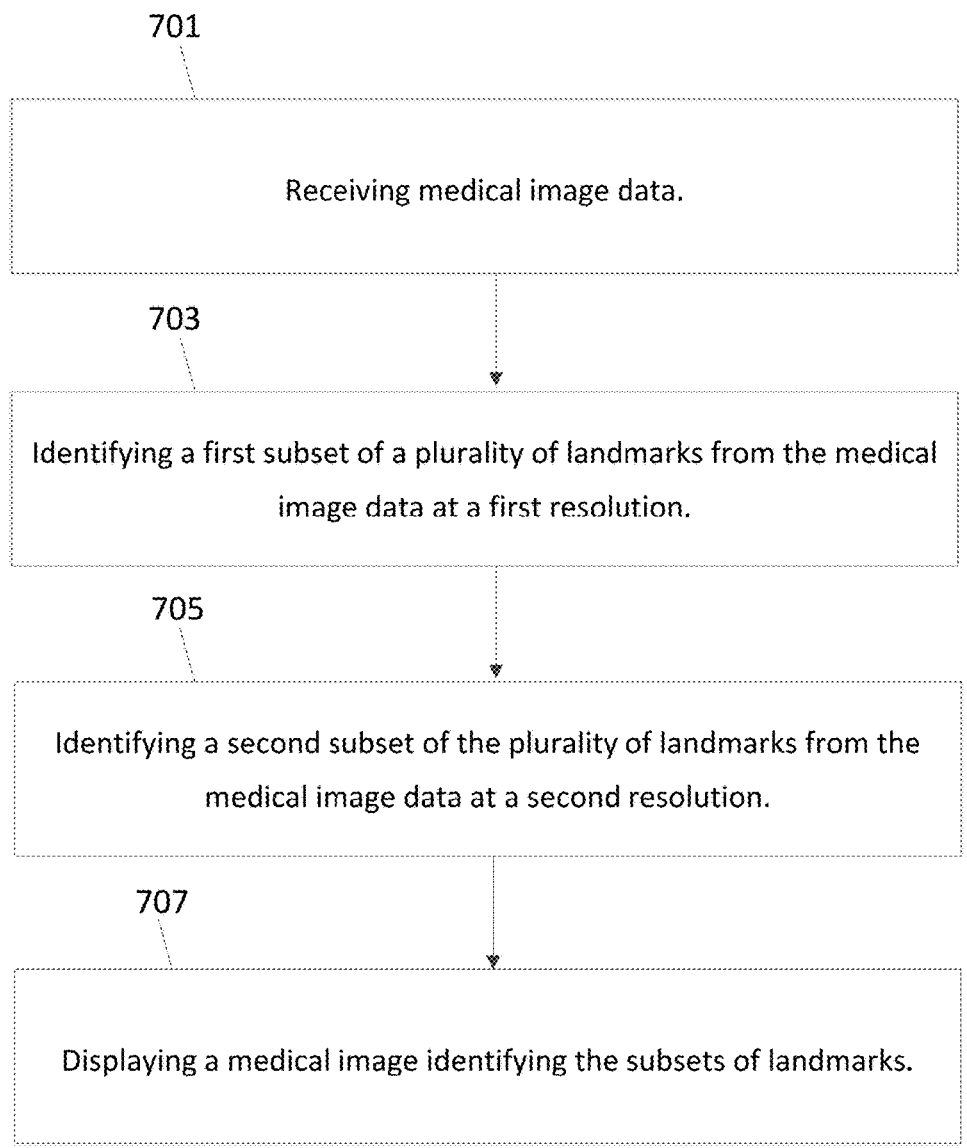
FIG. 7 illustrates a flowchart diagram of an embodiment of a method of multiple landmark detection.

FIG. 7 illustrates a flowchart diagram of an embodiment of a method of multiple landmark detection. The method is implemented by the system of FIG. 8 (discussed below), FIG. 9 (discussed below) and/or a different system. Additional, different or fewer acts may be provided. For example, the acts 707 may be omitted to when no landmark detected. The method is provided in the order shown. Other orders may be provided and/or acts may be repeated. For example, acts 703 and 705 may be repeated to detect additional landmarks at a different resolution. Acts 701, 703, 705 and/or 707 may also be repeated to detect landmarks from another test image.

At act 701, medical image data is received. For example, the medical image data may be received from a medical scanner. The medical image data is two-dimensional image data, with each pixel as a potential landmark of a plurality of landmarks. Alternatively, the medical image data is three-dimensional image data, with each voxel as a potential landmark of a plurality of landmarks. For example, the test image may be a CT or MRI image of a patient for a clinical task, such diagnosis, surgical planning, postoperative assessment, etc. Other imaging modalities may be used. The test image is captured using the same imaging modality as was used during training of the first and second learned neural networks used in acts 703 and 705.

At act 703, a first subset of a plurality of landmarks are identified from the medical image data at a first resolution. The first subset of a plurality of landmarks is identified using a first learned deep neural network. Referring back to FIG. 5, landmarks 501, 503, 505 and 507 are identified using the first trained deep neural network. The landmarks are identified based on the appearance of the landmarks and the spatial configuration between the landmarks (e.g., denoted by the example lines connecting the landmarks). For example, landmark 501 is identified using the relative location of landmark 503. Landmark 503 is identified using the relative locations of landmarks 501 and 505. Landmark 505 is identified using the relative locations of landmarks 503 and 507. Landmark 507 is identified using the relative location of landmark 505. In this example, the relative locations of landmarks 501 and 507 are not used because they may not be useful in predicting the location of one another. Any combination of landmark 501-507 may be used for relative location. The relative location may not be sequential, instead being simultaneous (e.g., 501 being found based on 503 and 507 and 503 being found based on 501 and 505).

Referring back to FIG. 7, at act 705, a second subset of a plurality of landmarks are identified from the medical image data at a second resolution. The second subset of a plurality of landmarks is identified using a second learned deep neural network. The second resolution is higher (e.g., finer) than the first, coarser resolution. The first subset of landmarks may include fewer landmarks than the second subset of landmarks.

In an embodiment, the locations of the first subset of landmarks are used to identify the second subset of landmarks. Referring back to FIG. 5 and FIG. 6, the location of landmark 501 is used to identify landmarks 601, 603, 605 and 607. The location of landmarks 503 and 505 are used to identify landmarks 617, 619, 621, 623, 625 and 627. The location of landmark 507 is used to identify landmarks 611, 612 and 615. The number landmarks in the first subset of landmarks (e.g., FIG. 5) and the number of landmarks in the second subset of landmarks (e.g., FIG. 6) are selected such that identifying the first subset of landmarks and identifying the second subset of landmarks requires substantially the same computational complexity. For example, the computational complexity of identifying landmarks 501, 503, 505 and 507 is substantially the same as one of the following subsets: 601-607; 611-615; or 617-627.

At act 707, a medical image is displayed identifying the subsets of landmarks. For example, the result of the landmark detection is displayed to the user, such as by displaying a two-dimensional rendered image or three-dimensional volume rendering with multiple landmarks depicted and labeled (e.g., annotation, arrows, highlighting with brightness and/or color, or other indicator of the landmark location). Alternatively or additionally, the landmarks are used for registration or spatial alignment between different sets of imaging data (e.g., different imaging modalities and/or imaging data from different times for the same patient). The images, as aligned, may be combined and displayed or displayed side-by-side. The medical image may be used for clinical tasks, such diagnosis, surgical planning, postoperative assessment, etc.

Figure 8:
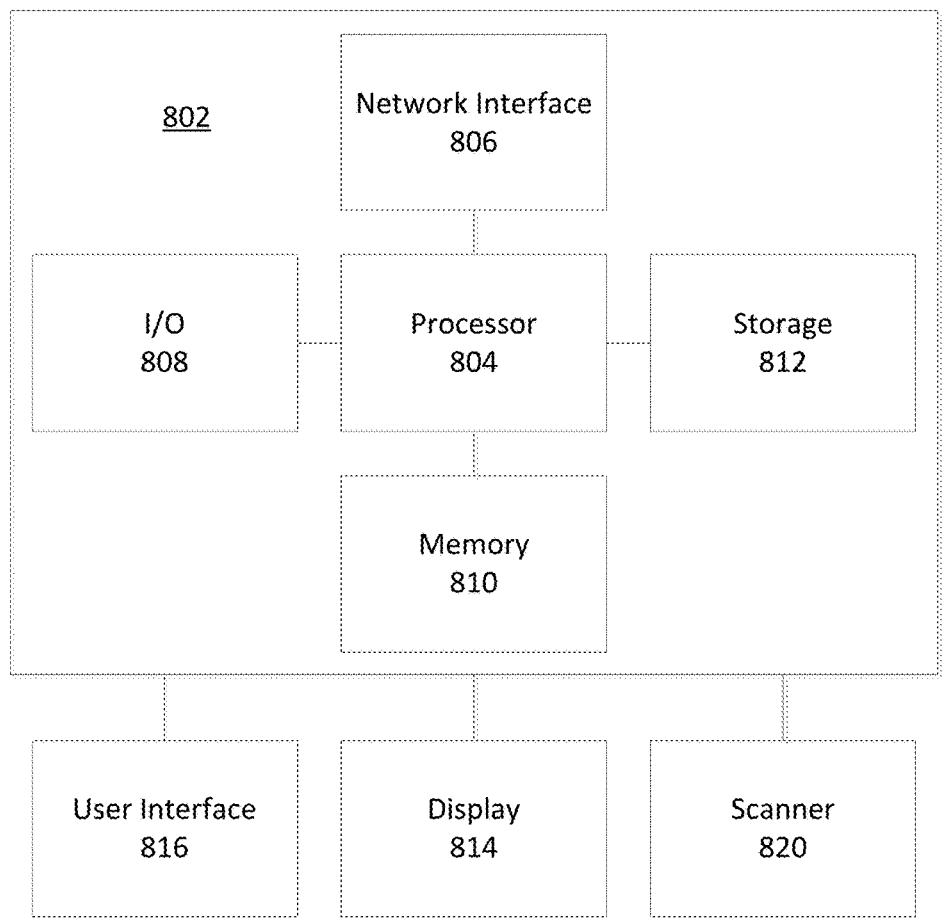
FIG. 8 illustrates an embodiment of a system for detecting multiple landmarks in medical image data.

FIG. 8 illustrates an embodiment of a system for detecting multiple landmarks in medical image data. For example, the system is implemented on a computer 802. A high-level block diagram of such a computer 802 is illustrated in FIG. 8. Computer 802 includes a processor 804, which controls the overall operation of the computer 802 by executing computer program instructions which define such operation. The computer program instructions may be stored in a storage device 812 (e.g., magnetic disk) and loaded into memory 810 when execution of the computer program instructions is desired. The memory 810 may be local memory as a component of the computer 802, or remote memory accessible over a network, such as a component of a server or cloud system. The acts of the methods illustrated in FIG. 1 and FIG. 7 may be defined by the computer program instructions stored in the memory 810 and/or storage 812, and controlled by the processor 804 executing the computer program instructions. A scanner 820 is an image acquisition device such as a two-dimensional or three-dimensional scanner, and may be connected to the computer 802 for receipt of a test image by the computer 802. It is also possible to implement the scanner 820 and the computer 802 as a single device. It is further possible that the scanner 820 and the computer 802 communicate wirelessly or with wired connection through a network.

The scanner 820 is any image acquisition device for capturing medical image data. The scanner 907 may use any imaging modality, such as computed tomography (CT), magnetic resonance (MR), ultrasound, x-ray, angiography, fluoroscopy, positron emission tomography, single photon emission computed tomography, or others. Other types of scanners may be used. The scanner may capture two-dimensional image data (e.g., pixels) or three-dimensional image data (e.g., voxels).

The computer 802 also includes one or more network interfaces 806 for communicating with other devices via a network, such as the scanner 820. The computer 802 includes other input/output devices 808 enabling user interaction with the computer 802, such as using user interface 816 and display 814. The user interface 816 may be a keyboard, mouse, speakers, buttons, etc. The display 814 may communicate information to a user and may display medical images and the detected landmarks for clinical tasks, such pathological diagnosis, surgical planning, post-operative assessment, etc. The input/output devices 808 may be used in conjunction with a set of computer programs, such as landmark detection tools for detecting landmarks in medical images received from the scanner 820. One skilled in the art will recognize that an implementation of an actual computer could contain other components as well, and that FIG. 8 is a high level representation of some of the components of such a computer for illustrative purposes.

The computer 802 may be used to implement a system for detecting multiple landmarks in medical image data. Storage 812 stores a plurality training images. The training images may have landmarks annotated for machine learning (e.g., ground truth data). Processor 804 executes computer program code stored on memory 810 to receive the plurality of a plurality of training images and to train a machine learning artificial agent to detect landmarks from medical images. For example, the machine learning artificial agent is a deep neural network. Other machine learning artificial agents may be used. Using the plurality of training images, the processor 804 trains a first artificial agent to detect multiple landmarks at a first resolution of the training images. The processor 804 also trains a second artificial agent to detect multiple landmarks at a second resolution of the training images. For example, using a deep neural network, training the artificial agents includes simultaneously learning convolutional layers of the artificial agents to extract features from the plurality of training images and learning convolutional layers of the artificial agents to map spatial relationships between features of the plurality of training images.

Processor 804 also executes computer program code stored on memory 810 to detect landmarks in a medical image using the trained artificial agents. For example, the processor 804 receives medical image data captured by the scanner 820. The learnt neural networks or trained agents are stored in the memory 810, such as matrices. Using the received medical image data, the processor 804 detects multiple landmarks from the medical image data using the trained artificial agents. The processor 804 detects landmarks iteratively at different resolutions, such as detecting a first set of landmarks at a lower resolution with a first artificial agent, then detecting a second set of landmarks at a higher resolution with a second artificial agent. The processor 804 may detect multiple landmarks from the medical image data in response to a request received from the user interface 816. The result of the landmark detection is displayed to the user with display 814, such as a two-dimensional image or three-dimensional volume rendering with multiple landmarks displayed to the user.

Figure 9:
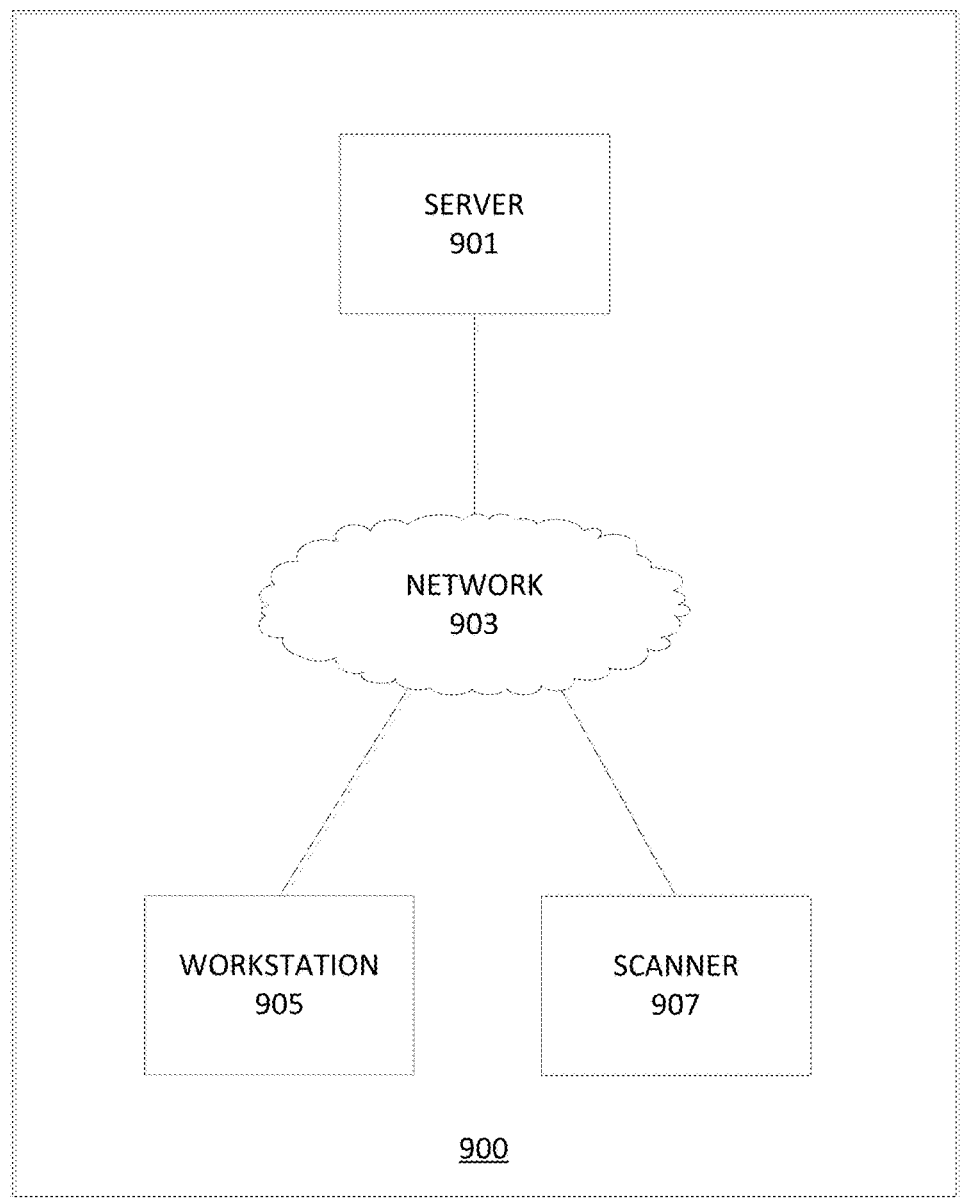
FIG. 9 illustrates another embodiment of a system for detecting multiple landmarks in medical image data.

FIG. 9 illustrates another embodiment of a system for detecting multiple landmarks in medical image data. The system trains for detecting and/or detects multiple landmarks in a medical image using one or both of a workstation 905 and/or a remote server 901 using medical image training data and/or medical image test data, such as image data captured using scanner 907. In an example, the remote server 901 receives that a test image and performs imaging processing to detect multiple landmarks using the received test image. The workstation 905 displays the test image and the detected landmarks received from the remote server 901.

The system 900, such as a cloud-based imaging processing system, may include one or more of a server 901, a network 903, a workstation 905 and a scanner 907. Additional, different, or fewer components may be provided. For example, additional servers 901, networks 903, workstations 905 and/or scanners 907 may be used. In an example, the server 901 and the workstation 905 are directly connected, and may be implemented on a single computing device. In yet another example, the server 901, the workstation 905 and the scanner 907 are implemented on a single medical imaging device. As another example, the workstation 905 is part of the scanner 907, and the server 901 is a cloud-based server. In yet another embodiment, the scanner 907 performs the image capture and landmark detection without the network 903, server 901, or workstation 905.

The scanner 907 any type of two-dimensional or three-dimensional scanner. The scanner 907 may use any imaging modality, such as computed tomography (CT), magnetic resonance (MR), ultrasound, x-ray, angiography, fluoroscopy, positron emission tomography, single photon emission computed tomography, or others. Other types of scanners may be used. The scanner may capture two-dimensional image data (e.g., pixels) or three-dimensional image data (e.g., voxels). For example, the medical image data is captured by scanner 907 and stored on workstation 905 and/or server 901 via network 903.

The network 903 is a wired or wireless network, or a combination thereof. Network 903 is configured as a local area network (LAN), wide area network (WAN), intranet, Internet and/or other now known or later developed network configurations. Any network or combination of networks for communicating between the workstation 905, the scanner 907, the server 901 and any other system components.

The server 901 and/or workstation 905 is a computer platform having hardware such as one or more central processing units (CPU), a system memory, a random access memory (RAM) and input/output (I/O) interface(s). The server 901 and workstation 905 also includes a graphics processor unit (GPU) to accelerate image rendering. The server 901 and workstation 905 are implemented on one or more server computers and/or client computers connected to network 903. Additional, different or fewer components may be provided. For example, an image processor and/or image rendering engine may be provided with one or more of the server 901, workstation 905, another computer or combination thereof (e.g., as hardware and/or software).

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

We claim:

1. A method of deep learning for multiple landmark detection, the method comprising:
receiving a plurality of training images;
training a first deep neural network at a first resolution of the training images, the training of the first deep neural network comprising:
learning locations of a first plurality of landmarks; and
learning the spatial relationships between the locations of the first plurality of landmarks;
training a second deep neural network at a second resolution of the training images, the training of the second deep neural network comprising:
learning locations of a second plurality of landmarks; and
learning spatial relationships between the locations of the second plurality of landmarks;
wherein the locations of the second plurality of landmarks are learnt at the second resolution based on the locations of the first plurality of landmarks at the first resolution.

2. The method of claim 1, further comprising:
receiving a test image;
detecting, using the first trained deep neural network, the locations of the first plurality of landmarks at a first resolution of the test image; and
detecting, using the second trained deep neural network, the locations of the second plurality of landmarks at a second resolution of the test image.

3. A method of deep learning for multiple landmark detection, the method comprising:
receiving a plurality of training images;
training a first deep neural network at a first resolution of the training images, the training of the first deep neural network comprising:
learning locations of a first plurality of landmarks; and
learning the spatial relationships between the locations of the first plurality of landmarks;
training a second deep neural network at a second resolution of the training images, the training of the second deep neural network comprising:
learning locations of a second plurality of landmarks; and
learning spatial relationships between the locations of the second plurality of landmarks;
wherein training the first deep neural network comprises simultaneously learning a plurality of landmark probability maps for the first plurality of landmarks and training the second deep neural network comprises simultaneously learning a plurality of landmark probability maps for the second plurality of landmarks.

4. The method of claim 3, wherein a different landmark probability map is learned for each landmark.

5. The method of claim 3, wherein simultaneously learning the plurality of landmark probability maps for the first plurality of landmarks and simultaneously learning the plurality of landmark probability maps for the second plurality of landmarks comprises message passing between landmark probability maps of neighboring landmarks.

6. The method of claim 5, wherein message passing between landmark probability maps of neighboring landmarks is configured to compensate for missing response information in each of the landmark probability maps.

7. A method of deep learning for multiple landmark detection, the method comprising:
receiving a plurality of training images;
training a first deep neural network at a first resolution of the training images, the training of the first deep neural network comprising:
learning locations of a first plurality of landmarks; and
learning the spatial relationships between the locations of the first plurality of landmarks;
training a second deep neural network at a second resolution of the training images, the training of the second deep neural network comprising:
learning locations of a second plurality of landmarks; and
learning spatial relationships between the locations of the second plurality of landmarks;
wherein the first deep neural network and the second deep neural network each comprise:
one or more convolutional layers configured to extract features from the training images; and
a convolutional layer configured to map the spatial configuration of the features,
wherein the convolutional layers are trained simultaneously.

8. The method of claim 7, wherein learning the locations of the first plurality of landmarks comprises learning an appearance of each of the first plurality of landmarks.

9. A system for detecting multiple landmarks in medical image data, the system comprising:
a scanner configured to capture medical image data;
at least one processor; and
at least one memory including computer program code for one or more programs, the at least one memory and the computer program code configured to, with the at least one processor, cause the system to:
receive the medical image data captured by the scanner;
detect, using a trained first artificial agent and a trained second artificial agent, multiple landmarks in the medical image data at different resolutions of the medical image data;
wherein the first artificial agent and the second artificial agent comprise:
convolutional layers of the artificial agents having been trained to extract features from the medical image data; and
convolutional layers of the artificial agents having been trained to map spatial relationships between features of the medical image data.

10. The system of claim 9, wherein the trained first artificial agent and the trained second artificial agent are deep neural networks.

11. The system of claim 9, wherein the convolutional layers comprise layers having been trained simultaneously.

12. The system of claim 9, wherein the at least one memory and the computer program code is further configured to, with the at least one processor, cause the system to:
receive a plurality of a plurality of training images; and
train, based on the plurality of training images, the first artificial agent to detect multiple landmarks at a first resolution and the second artificial agent to detect multiple landmarks at a second resolution.

13. A method for multiple landmark detection, the method comprising:
receiving, from a medical scanner, medical image data;
identifying, using a first learned deep neural network, a first subset of a plurality of landmarks from the medical image data at a first resolution;
identifying, using a second learned deep neural network, a second subset of the plurality of landmarks from the medical image data at a second resolution; and displaying a medical image from the medical image data identifying the identified first subset of landmarks and the identified second subset of landmarks;

wherein locations of the first subset of landmarks are used to identify the second subset of landmarks.

14. The method of claim 13, wherein the medical image data is two-dimensional image data, and wherein each pixel is one landmark of the plurality of landmarks.

15. The method of claim 13, wherein the medical image data is three-dimensional image data, and wherein each voxel is one landmark of the plurality of landmarks.

16. The method of claim 13, wherein the first resolution is lower than the second resolution, and wherein the first subset of landmarks includes fewer landmarks than the second subset of landmarks.

17. A method for multiple landmark detection, the method comprising:

receiving, from a medical scanner, medical image data;

identifying, using a first learned deep neural network, a first subset of a plurality of landmarks from the medical image data at a first resolution;

identifying, using a second learned deep neural network, a second subset of the plurality of landmarks from the medical image data at a second resolution; and displaying a medical image from the medical image data identifying the identified first subset of landmarks and the identified second subset of landmarks;

wherein a first number landmarks in the first subset of landmarks and a second number of landmarks in the second subset of landmarks are selected such that identifying the first subset of landmarks and identifying the second subset of landmarks requires substantially the same computational complexity.

* * * * *